United States Patent
Morley et al.

(10) Patent No.: US 9,411,929 B2
(45) Date of Patent: Aug. 9, 2016

(54) METHOD OF DETERMINING RNA INTEGRITY

(71) Applicant: Monoquant Pty. Ltd., Adelaide (AU)

(72) Inventors: Alexander Alan Morley, Malvern (AU); Michael Julian Brisco, Campbelltown (AU)

(73) Assignee: MONOQUANT PTY. LTD. (AU)

( * ) Notice: Subject to any disclaimer, the term of this patent is extended or adjusted under 35 U.S.C. 154(b) by 0 days.

(21) Appl. No.: 13/868,889

(22) Filed: Apr. 23, 2013

(65) Prior Publication Data

US 2013/0309680 A1 Nov. 21, 2013

Related U.S. Application Data

(60) Provisional application No. 61/637,253, filed on Apr. 23, 2012.

(51) Int. Cl.
*C12Q 1/68* (2006.01)
*G06F 19/20* (2011.01)
*G06F 19/10* (2011.01)

(52) U.S. Cl.
CPC .............. *G06F 19/20* (2013.01); *C12Q 1/6809* (2013.01); *C12Q 1/6851* (2013.01); *C12Q 1/6886* (2013.01); *C12Q 2537/165* (2013.01); *G06F 19/10* (2013.01)

(58) Field of Classification Search
None
See application file for complete search history.

(56) References Cited

FOREIGN PATENT DOCUMENTS

| WO | WO 97/02361 A1 | 9/2004 |
|----|----------------|--------|
| WO | WO 2004/079005 A1 | 9/2004 |
| WO | WO 2005/090609 A1 | 9/2005 |
| WO | WO 2010/025447 A1 | 3/2010 |
| WO | WO 2013/159145 A1 | 10/2013 |

OTHER PUBLICATIONS

Schroeder et al. The RIN: an RNA integrity number for assigning integrity values to RNA measurements. BMC Molec. Biol. (2006) vol. 7, No. 3, pp. 1-14.*
Auer et al, "Chipping away at the chip bias: RNA degradation in microarray analysis," Nature Genetics, 35(4):292-293, (2003).
Brisco et al "Incorporation of measurement of DNA integrity into qPCR assays," Biotechniques, 49:893-897, (2010).
Brisco et al, "Quantification of RNA integrity and its use for measurement of transcipt number," Nucleic Acids Research, 40(18):e144, 9 pages, doi:10.1093/nar/gks588, (2012). (published online; downloaded from http://nar.oxfordjournals on Jul. 16, 2013).
Gong et al., "Quantification of RNA damage by reverse transcription polymerase chain reactions," Anal. Biochem., 357:58-67, (2006).
Ho-Pun-Cheung et al, "Reverse transcription-quantitative polymerase chain reaction: description of a RIN-based algorithm for accurate data normalization," BMC Mol. Biol., 10:31-40, (2009).
Swift et al, "Assessment of RNA quality by semi-quantitative RT-PCR of multiple regions of a long ubiquitous mRNA," BioTechniques, , 28:524-531, (2000).
WIPO Application No. PCT/AU2013/000422, International Preliminary Report on Patentability, mailed Nov. 6, 2014.
WIPO Application No. PCT/AU2013/000422, International Search Report, mailed Jul. 2, 2003.
WIPO Application No. PCT/AU2013/000422, Written Opinion of the International Searching Authority, mailed Jul. 2, 2003.
CN Application No. CN 201380029890.2, Notification of First Office Action, mailed Dec. 4, 2015.
EPO Application No. EP 13782246.6, Supplementary European Search Report and European Search Opinion, mailed Nov. 5, 2015.

* cited by examiner

*Primary Examiner* — David Thomas
(74) *Attorney, Agent, or Firm* — Alston & Bird LLP

(57) ABSTRACT

A method of determining a quantitative measure of the integrity of RNA in a sample, the method comprising: (i) assaying a sample containing instances of an RNA molecule transcribed from a reference gene, at least some of the instances being damaged, to determine quantitative measures of the relative or absolute numbers of intact instances of each of a plurality of segments of the RNA molecule in the sample, the segments having respective different lengths; (ii) based on a relationship between the determined quantitative measures and the respective different lengths of the segments, determining a quantitative measure of integrity of the instances of the RNA molecule in the sample; and (iii) determining the total number of instances of an RNA molecule of interest in a sample by using the quantitative measure of integrity and the length of a corresponding degradation-relevant segment of the RNA molecule of interest.

13 Claims, 6 Drawing Sheets

METHOD OF DETERMINING RNA INTEGRITY

CROSS REFERENCE TO RELATED APPLICATIONS

This application claims the benefit under 35 USC 119(e) of U.S. Provisional Patent Application No. 61/637,253, filed Apr. 23, 2012, which is incorporated herein by reference in its entirety for all purposes.

FIELD OF THE INVENTION

The present invention relates to a method of quantifying RNA integrity in a biological sample and, more particularly, to a method of quantifying mRNA integrity. The method of the present invention facilitates not only quantification of RNA integrity in a sample of interest, but also provides a means of correcting the results of quantification of mRNA expression to take account of the extent of RNA degradation. The method of the present invention is useful in a range of applications including, but not limited to, providing a means to more accurately determine mRNA expression levels, such as in the context of diagnosing or monitoring conditions characterised by changes to mRNA levels.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The accuracy of gene expression evaluation is influenced by the quantity and quality of starting RNA. Purity and integrity of RNA are critical elements for the overall success of RNA-based analyses. Starting with low quality RNA may strongly compromise the results of downstream applications which are often labour-intensive, time-consuming and highly expensive. It is therefore preferable to use high-quality intact RNA as a starting point in molecular biological as well as in diagnostic applications. The integrity of RNA should be checked in applications such as quantitative RT-PCR, RNA sequencing, micro-arrays, ribonuclease-protection-assay, in situ hybridization, northern blot analysis, RNA mapping, in vitro translation, cDNA library construction and any kind of sequencing or array applications. This issue is particularly important in clinical applications with unique or limited tissue material, (for example, tissue obtained after surgery), where a reliable RNA quantification is required.

To date, there have been methods developed which enable one to assess the quality of an RNA population of interest in order to determine whether it is of sufficient quality to use for analysis purposes. For example, to determine the purity of RNA, the $OD_{260nm}/OD_{280nm}$ ratio can be taken into account, although this parameter only provides information about protein or phenol contamination, and does not give appropriate and full information about RNA integrity. For decades, the only way to determine the degradation level of RNA was the use of agarose gel-based electrophoresis, but this method is variable, inaccurate, time consuming and cost intensive.

Several methods for assessing RNA integrity are based on measuring the number of different RNA species, of the same or different lengths, or different segments of the same RNA species, and deriving a number which is related to RNA integrity. The best example is the 3':5' method which measures by PCR the Cq values obtained from amplification of a 3' and a 5' segment of an RNA molecule and uses the ratio of amplicon numbers so obtained as a measure of RNA integrity.

Automated platforms for the assessment of RNA quality are also used. Currently, two automated systems are available for this purpose: the Experion (Bio-Rad Laboratories, Hercules, Calif., USA), and the 2100 Bioanalyzer (Agilent Technologies, Palo Alto, Calif., USA). Both systems are based on an automated and miniaturized electrophoresis system, realized by Lab-on-chip technology. Both platforms determine RNA quality by using either the ribosomal 28S/18S ratio, or a numerical system which represents the integrity of RNA. Agilent Technologies offers the RIN algorithm (RNA Integrity Number) on the 2100 Bioanalyzer, and Bio-Rad recently developed a new Experion software version that offers an algorithm for calculating the RNA Quality Index (RQI). The RIN and the RQI are based on a numbering system from 1 to 10, with 1 being the most degraded RNA profile and 10 being the most intact.

However, all of the above means of assessing RNA integrity only provide a measurement on an ordinal scale: although they can rank the integrity of different samples relative to one another or to an external standard, they provide a qualitative rather than a truly quantitative measure. The number or assessment that they provide may be sufficient to indicate whether or not the integrity of RNA in a sample is sufficient to permit its further analysis, but their utility is largely limited to this purpose. What is needed is a method for measurement of RNA integrity on a ratio scale; i.e., a truly quantitative method, one which relates to the structure of RNA and enables measurements of an RNA molecule of interest to be combined with a measurement of RNA degradation to produce a quantitative measurement of the total number of the RNA molecule of interest. To date, there has been no means of achieving this.

In work leading up to the present invention, there has been developed a method for quantifying the degree of integrity of an RNA sample. More specifically, the integrity of RNA in a sample is quantified in terms of the probability that a nucleotide is damaged. This quantitative information is useful both in its own right and for use in correcting, for the degree of degradation, subsequently obtained RNA expression results.

The method of the present invention therefore has a wide range of potential applications both in terms of quantifying RNA integrity, per se, in a biological sample and, further, in terms of enabling the correction, and thereby accurate quantification, of mRNA expression levels of a specific RNA genus of interest. In terms of diagnostic and prognostic applications which rely on an analysis of changes to RNA levels, such as mRNA levels, the development of the present method now enables one to achieve a level of accuracy not previously available, and thereby overcomes currently existing diagnostic and prognostic limitations in relation to the utility of RNA data previously generated.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of determining a quantitative measure of the integrity of RNA in a sample, said method comprising:
(i) assaying a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths; and
(ii) based on a relationship between the determined quantitative measures and the respective different lengths of said segments, determining a quantitative measure of integrity of the instances of said RNA molecule in said sample. In some embodiments, the method may further comprise:
(iii) quantifying the RNA of interest and correcting this result using the measure of integrity calculated in step (ii) and the length of a corresponding degradation-relevant segment (or derivative thereof) of the RNA of interest.

In some embodiments, the method may further comprise:
(iii) quantifying the RNA transcribed from a gene of interest transcribed from a standard gene and correcting this result using the measure of integrity determined in step (ii) and the length of a corresponding degradation-relevant segment (or derivative thereof) of the RNA of interest.

In a related aspect, there is provided a method of quantifying an RNA of interest, said method comprising:
(i) assaying a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths;
(ii) based on a relationship between the determined quantitative measures and the respective different lengths of said segments, determining a quantitative measure of integrity of the instances of the RNA molecule in said sample;
(iii) quantifying the RNA of interest and correcting this result using the measure of integrity calculated in step (ii) and the length of a degradation-relevant segment of the RNA of interest.

In another aspect there is provided a method for quantifying a measure of the integrity of mRNA in a sample, said method comprising:
(i) assaying a sample containing instances of an mRNA molecule transcribed from a reference gene, at least some of said instances being damaged, to determine quantitative measures of the relative or absolute numbers of intact instances of each of a plurality of segments of said mRNA molecule in said sample, said segments having respective different lengths; and
(ii) based on a relationship between the determined quantitative measures and the respective different lengths of said segments, determining a quantitative measure of integrity of the instances of the mRNA molecule in said sample.

In still another aspect there is provided a method of quantifying an mRNA of interest, said method comprising:
(i) assaying a sample containing instances of an mRNA molecule transcribed from a reference gene, at least some of said instances being damaged, to determine quantitative measures of the relative or absolute numbers of intact instances of each of a plurality of segments of said mRNA molecule in said sample, said segments having respective different lengths;
(ii) based on a relationship between the determined quantitative measures and the respective different lengths of said segments, determining a quantitative measure of integrity of the instances of the mRNA molecule in said sample.
(iii) quantifying the mRNA of interest and correcting this result using the measure of integrity calculated in step (ii) and the length of a degradation-relevant segment of the RNA of interest.

The relationship between N, the number of instances of said RNA molecule in said sample, $N_i$, the quantitative measures of the relative or absolute numbers of intact instances of each of a plurality of segments i of said RNA molecule in said sample, $L_i$, the lengths of said segments, and the mean number r of lesions per nucleotide of the instances of the RNA molecule may be given by:

$$N_i = N \cdot e^{-L_i \cdot r}$$

The linear relationship may be represented as:

$$\ln(N_i) = \ln(N) - L_i \cdot r$$

so that the value of r is determined as the gradient of the linear relationship between $\ln(N_i)$ and $L_i$.

In yet another aspect, there is provided a method of quantifying the RNA transcribed from a gene of interest, said method comprising:
(i) assaying a sample containing instances of an RNA molecule transcribed from a reference gene, at least some of said instances being damaged, to determine quantitative measures of relative or absolute numbers of intact instances of each of a plurality of segments of said RNA molecule in said sample, said segments having respective different lengths;
(ii) based on a relationship between the determined quantitative measures and the respective different lengths of said segments, determining a quantitative measure of integrity of the instances of the RNA molecule in said sample;
(iii) quantifying the RNA transcribed from a gene of interest transcribed from a standard gene and correcting this result using the measure of integrity calculated in step (ii) and the length of a segment of the RNA of interest.

To the extent that quantification of the amount of the RNA molecule of interest is relative to quantification of a standard RNA, the amount of the RNA molecule of interest in the sample relative to the amount of the standard RNA molecule is given by:

$$N_{test}/N_{stan} = (S_{test}/S_{stan}) \cdot e^{(L_{test} \cdot r_{test} - L_{stan} \cdot r_{stan})}$$

where $N_{test}/N_{stan}$ is the ratio of the amount of the RNA molecule of interest (test molecule) to the amount of the standard RNA molecule, $S_{test}/S_{stan}$ is the ratio of the measured amounts of the respective test and standard segments in the sample, $L_{test}$ and $L_{stan}$ are the respective are lengths of the test and standard degradation-relevant segments, and $r_{test}$ and $r_{stan}$ are the mean number r of lesions per nucleotide of the instances of the test and standard RNA molecules in the samples in which they are contained.

In yet another aspect, there is provided a method for use in determining a quantitative measure of the integrity of RNA in a sample, said method comprising:
(i) accessing RNA expression profiling data representing standard quantification of at least one RNA molecule;

(ii) accessing RNA integrity data representing a quantitative measure of integrity of the instances of each said RNA molecule;

(iii) accessing length data representing one or more lengths of respective degradation-relevant segments (or derivatives thereof) of the RNA molecule; and (iv) processing the RNA expression profiling data, the RNA integrity data and the length data to generate corrected RNA expression profiling data representing corrected values of said quantification of said at least one RNA molecule.

In yet another aspect, there is provided a method for use in determining a quantitative measure of the integrity of RNA in a sample, said method comprising:
(i) assaying a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths, to generate assay data representing said quantitative measures and said lengths; and
(ii) processing said assay data to generate integrity data representing a quantitative measure of integrity of the instances of said RNA molecule in said sample, based on a relationship between the determined quantitative measures and the respective different lengths of said segments.

In some embodiments, the method further comprises:
(iii) quantifying the RNA of interest; and
(iv) correcting the result of said quantifying using the measure of integrity determined in step (ii) and the length of a corresponding degradation-relevant segment (or derivative thereof) of the RNA of interest.

In some embodiments, said RNA is mRNA.

In some embodiments, each length has a constant component and a variable component. In some embodiments, each length is a statistical average of a plurality of different lengths.

In yet another aspect, there is provided an RNA expression profiling system, comprising one or more RNA integrity components configured to:
(i) access RNA expression profiling data representing standard quantification of at least one RNA molecule;
(ii) access RNA integrity data representing a quantitative measure of integrity of the instances of each said RNA molecule;
(iii) access length data representing one or more lengths of corresponding degradation-relevant segments (or derivatives thereof) of the RNA molecule; and
(iv) process the RNA expression profiling data, the RNA integrity data and the length data to generate corrected RNA expression profiling data representing corrected values of said quantification of said at least one RNA molecule.

In some embodiments, the RNA integrity components are further configured to:
(i) assay a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths, to generate assay data representing said quantitative measures and said lengths; and
(ii) process said assay data to generate integrity data representing a quantitative measure of integrity of the instances of said RNA molecule in said sample, based on a relationship between the determined quantitative measures and the respective different lengths of said segments.

DETAILED DESCRIPTION OF THE INVENTION

Figure 1:
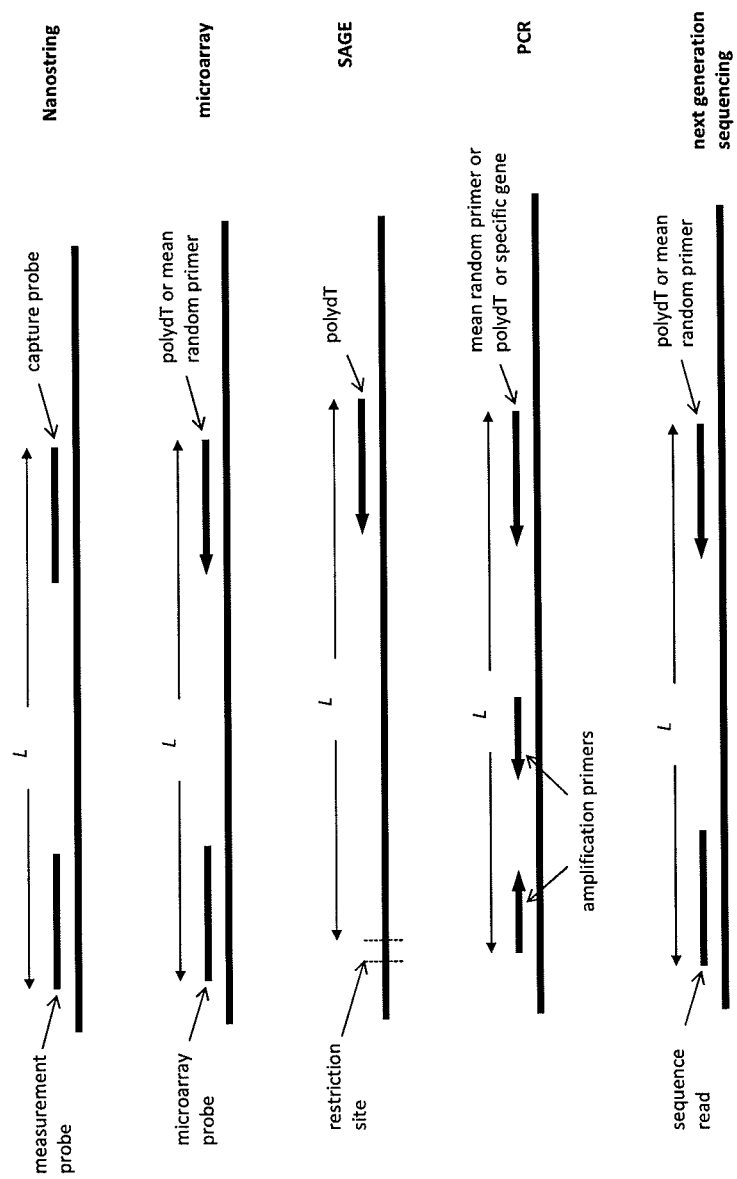
FIG. 1. Illustration of the length L of the critical degradation-relevant segment within which a degrading lesion will affect quantification of an RNA of interest and without (i.e., outside of) which a degrading lesion will not affect said quantification. The critical segment depends on the method of quantification and is shown for quantification by nanostring, microarray, SAGE, nucleic acid amplification as exemplified by PCR, and next generation sequencing. The length of the critical segment is L bases. Note that the critical segment is conceptually and often practically different to the region of RNA or its cDNA derivative which is used in the final step of quantification.

The present invention is predicated, in part, on the development of a means to quantify RNA integrity based on determining the probability that an RNA base in a biological sample of interest is damaged. This development has enabled, for the first time, both significantly more accurate quantification of RNA integrity in a sample of interest and further, the ability to use this information to correct, for the degree of degradation, a quantitative RNA expression level reading of a gene of interest from the same sample. The development of this method has enabled more informative and accurate RNA expression data to be obtained, thereby facilitating significant improvement to the utility of diagnostic, prognostic and therapeutic applications which rely on RNA expression information.

Accordingly, one aspect of the present invention is directed to a method of determining a quantitative measure of the integrity of RNA in a sample, said method comprising:
(i) assaying a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths; and
(ii) based on a relationship between the determined quantitative measures and the respective different lengths of said segments, determining a quantitative measure of integrity of the instances of said RNA molecule in said sample.

In a related aspect, there is provided a method of quantifying an RNA of interest, said method comprising:
(i) assaying a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths;
(ii) based on a relationship between the determined quantitative measures and the respective different lengths of said segments, determining a quantitative measure of integrity of the instances of the RNA molecule in said sample;
(iii) quantifying the RNA of interest and correcting this result using the measure of integrity calculated in step (ii) and the length of a degradation-relevant segment of the RNA of interest.

Reference to quantifying or obtaining a quantitative measure of an "RNA molecule" should be understood as quantifying or obtaining a quantitative measure of said RNA molecule directly or as quantifying or obtaining a quantitative measure of a derivative, such as cDNA, of said RNA molecule.

It should also be understood that the quantitative measure obtained for "said RNA in said sample" is the same for other species of RNA molecules in said sample.

Reference to the "measure of integrity" of the subject RNA is a reference to determining the extent of RNA degradation. It can be expressed as its complement or inverse. Without limiting the present invention to any one theory or mode of action, RNA is a very unstable molecule, unlike its DNA equivalent. The quality of RNA in a sample can vary widely from one type of sample to the next, and is impacted upon by a variety of physical and chemical factors such as heat, radiation, chemicals and tissue ribonucleases. Accordingly, not only is it easily degradable, but the extent of degradation can vary greatly between samples, thereby making it infeasible to assess and/or compare quantitative RNA expression data between samples, even if they are harvested from the same patient.

Reference to "quantifying or obtaining a quantitative measure" should be understood as obtaining a measure which is on a ratio scale. A measure of integrity on a ratio scale can be expressed as the number of lesions per RNA nucleotide (r), this figure being relevant both as an indicator of the integrity of the RNA in the sample tested, and for use to correct the quantified RNA expression results which may be obtained in relation to a separate gene of interest. The measure of integrity can also be expressed as a statistic which is mathematically equivalent to the number of lesions per RNA nucleotide. For example, if a region of interest of an RNA sequence is being considered and the length of the region is known, then the integrity of that RNA sequence can be expressed as the proportion of instances of that sequence which are intact.

Reference to "RNA" should be understood as a reference to ribonucleic acid or derivative or analogue thereof. In this regard, it should be understood to encompass all forms of RNA including mRNA, primary RNA, rRNA, tRNA, microRNA and the like. The RNA of the present invention may be of any origin, including naturally occurring (such as would be derived from a biological sample harvested from a patient), recombinantly produced (such as a sample harvested from an in vitro culture sample), or synthetically produced.

Reference to "derivatives" should be understood to include reference to fragments, homologs or orthologs of said RNA from natural, synthetic or recombinant sources. The derivatives of said RNA sequences include fragments having particular regions of the RNA molecule fused to other proteinaceous or non-proteinaceous molecules. "Analogues" contemplated herein include, but are not limited to, modifications to the nucleotide or nucleic acid molecule such as modifications to its chemical makeup or overall conformation. This includes, for example, incorporation of novel or modified purine or pyrimidine bases or modification to the manner in which nucleotides or nucleic acid molecules interact with other nucleotides or nucleic acid molecules such as at the level of backbone formation or complementary base pair hybridisation. The biotinylation or other form of labelling of a nucleotide or nucleic acid molecules is an example of a "derivative" as herein defined. It would be appreciated that the derivatives and analogues described herein are unlikely to be observed in biological samples harvested from a patient, but may well be found in recombinantly or synthetically produced in vitro samples which are tested for their degree of integrity. "Derivative" of said RNA should also be understood to include the cDNA of said RNA.

In one embodiment, said RNA is mRNA.

According to this embodiment, there is provided a method for quantifying a measure of the integrity of mRNA in a sample, said method comprising:
(i) assaying a sample containing instances of an mRNA molecule transcribed from a reference gene, at least some of said instances being damaged, to determine quantitative measures of the relative or absolute numbers of intact instances of each of a plurality of segments of said mRNA molecule in said sample, said segments having respective different lengths; and
(ii) based on a relationship between the determined quantitative measures and the respective different lengths of said segments, determining a quantitative measure of integrity of the instances of the mRNA molecule in said sample.

In a related embodiment there is provided a method of quantifying an mRNA of interest, said method comprising:
(i) assaying a sample containing instances of an mRNA molecule transcribed from a reference gene, at least some of said instances being damaged, to determine quantitative measures of the relative or absolute numbers of intact instances of each of a plurality of segments of said mRNA molecule in said sample, said segments having respective different lengths;

(ii) based on a relationship between the determined quantitative measures and the respective different lengths of said segments, determining a quantitative measure of integrity of the instances of the mRNA molecule in said sample; and (iii) quantifying the mRNA of interest correcting this result using the measure of integrity calculated in step (ii) and the length of a degradation-relevant segment of RNA of interest.

In yet another embodiment, one might choose to analyse the primary RNA transcripts of a gene of interest.

The quantitative measure of integrity of the instances of the RNA molecule in said sample may represent the mean number of lesions per nucleotide of the instances of the RNA molecule.

The relationship may be represented as a linear relationship between the different lengths of said segments and logarithms of the respective determined quantitative measures, wherein the quantitative measure of integrity is determined from the gradient of the linear relationship. The gradient may be determined by regression.

Assuming that the lesions in RNA are distributed randomly as a result of independent random events whose distribution can be accurately represented using Poisson statistics, the relationship between N, the number of instances of said RNA molecule in said sample, $N_i$, the quantitative measures of the relative or absolute numbers of intact instances of each of a plurality of segments i of said RNA molecule in said sample, $L_i$, the lengths of said segments, and the mean number r of lesions per nucleotide of the instances of the RNA molecule may be given by:

$$N_i = N \cdot e^{-L_i r}$$

Taking natural logarithms of both sides, the linear relationship may therefore be represented as:

$$\ln(N_i) = \ln(N) - L_i \cdot r$$

so that the value of r is determined as the gradient of the linear relationship between $\ln(N_i)$ and $L_i$.

Reference to a "degradation-relevant segment" of RNA or its DNA derivative should be understood as reference to a region of an RNA or DNA molecule, said region being defined by the property that a lesion of any base within it will affect quantification of the RNA of interest, and a lesion of any base without (i.e., outside of) it will not affect said quantification. It will be appreciated that RNA in a sample may be subjected to a number of processes, such as capture or cDNA formation, which precede quantification, and that degrading lesions may affect the efficiency of such processes and thus affect the result of quantification, and that the region of RNA which "corresponds" to the sequence utilised in the method of the final quantification procedure may not correspond to the totality of the segment as hereinbefore defined.

Reference to "length" of a segment should be understood as reference to the number of nucleotides comprising that segment, and reference to the symbol "L" should be understood as reference to the length of the degradation-relevant segment.

The "degradation-relevant" segment as hereinbefore defined is illustrated in FIG. 1 in relation to different methods of quantification that may be used, the said methods involving various techniques of processing prior to the final step of measurement. The symbol "L" refers to the number of bases in the segment, and the horizontal arrows in the Figure illustrate the extent of the segment. The Figure also illustrates the region of RNA or its derivative which are used in the final quantification method, and it is evident that this region differs in extent from the segment as hereinbefore defined.

Reference to "the mean number r of lesions per nucleotide of the instances of the RNA molecule" should be understood as referring to both lesions already existing in the RNA at the time of sample collection, and lesions (referred to for brevity as processing lesions) produced during the process of RNA extraction, transport, storage, and measurement. Since RNA is relatively unstable as compared to DNA, processing lesions may comprise a significant proportion of lesions which affect the result of an RNA assay. For measurement assays involving reverse transcription of RNA to cDNA, processing lesions include lesions produced by the ribonuclease activity of reverse transcriptase, but lesions resulting from cDNA instability are effectively absent. If the number of already existing lesions per nucleotide is $r_a$ and the number of lesions per nucleotide produced during processing is $r_p$, then $$N_i = N \cdot e^{-L_i r_a} \cdot e^{-L_i r_p} = N \cdot e^{-L_i r}$$

where $r = r_a + r_p$

As detailed hereinbefore, the method of the present invention is predicated on determining the amount of intact RNA based on assaying a plurality of different lengths of RNA transcribed from a reference gene.

In this regard, it should be understood that the subject RNA may be assayed directly, or a cDNA version of this RNA may be first generated such that all subsequent assays are performed using the cDNA equivalent of the RNA of interest. Reference herein to "assaying" a plurality of segments should be understood to encompass both assaying the RNA directly or assaying a cDNA copy of the RNA.

The measure of integrity is determined in the context of a reference gene present in the sample of interest. Accordingly, the phrase "reference gene" should be understood to mean the gene or gene region which is used for the purpose of measuring integrity and the results from which can be applied to determining the integrity of the RNA of other genes. More particularly, the RNA transcribed from the reference gene is used for measuring integrity by quantifying a plurality of segments. To this end, the reference gene should be understood as a DNA molecule which undergoes transcription. The transcription product may or may not also undergo translation to a protein product. It would be appreciated by the person of skill in the art that not necessarily all RNA molecules are transcribed to protein. Whether or not the RNA molecule is one which undergoes translation to protein is irrelevant from the point of view of choosing a reference gene or even the gene of interest, since the present invention is directed only to quantifying the integrity of any type of RNA molecule. Some genes are known to produce an RNA transcription product but not also a protein translation product. In terms of chromosomal DNA, the gene may include both intron and exon regions. However, to the extent that the DNA of interest is cDNA, such as might occur if the DNA of interest is vector DNA, there may not exist intron regions. Such DNA may nevertheless include 5' or 3' untranslated regions. Accordingly, reference to "gene" herein should be understood to encompass any form of DNA which undergoes transcription including, for example, genomic DNA and cDNA. The subject "gene" may also be any region of genomic DNA produced by recombination, either between two regions of genomic DNA or one region of genomic DNA and a region of foreign DNA such as a virus or an introduced sequence. It may be a region of a partly or wholly synthetically or recombinantly generated nucleic acid molecule.

It will be appreciated that a plurality of reference genes can be used, and that either a plurality of measures of integrity can be obtained, or a single measure of integrity can be obtained, by considering all of the results of quantification obtained from all of the segments quantified. However it will be appreciated that the simplest approach would be to use one reference gene and obtain one measure of integrity.

Without limiting the present invention in any way, any gene can be selected for use as a reference gene, provided that the gene is that which undergoes transcription.

It is preferred that the gene is one that is highly expressed in the tissue being studied since this increases the sensitivity of the method. Examples of genes suitable for use as a reference gene include, but are not limited to, GAPDH, beta-actin, HPRT and β2 microglobulin. The cDNA derived from the RNA transcript of the reference gene may be produced by either random, polydT or gene-specific priming.

In some embodiments, the assaying includes cyclic amplification of a cDNA derivative of a sequence of each of the plurality of segments of said RNA molecule to a predetermined threshold, and the quantitative measure of integrity of the instances of the RNA molecule in said sample is determined from the relationship between the lengths $L_i$ of said segments and the respective numbers $Cq_i$ of amplification cycles required to meet the predetermined threshold.

In the context of this embodiment, the relationship may be represented as a linear relationship between the different lengths of said segments and the respective numbers of amplification cycles ($Cq_i$) required to meet the predetermined threshold, wherein the quantitative measure of integrity is determined from the gradient of the linear relationship. The gradient may be determined by regression.

The linear relationship in this embodiment may be represented as:

$$Cq_i = \text{constant} + L_i \cdot r / \ln(a_i)$$

where $a_i$ is the amplification efficiency per cycle of the $i^{th}$ segment. The value of $a_i$ can be determined for each segment of the reference RNA, but it is preferred to employ an efficient amplification system so that in practice all values of $a_i$ have the same value, $a$, which is known, and the relationship thus becomes:

$$Cq_i = \text{constant} + L_i \cdot r / \ln(a)$$

The method may include determining a quantitative measure of the relative or absolute number of instances of said RNA molecule in said sample, based on the quantitative measure of integrity of the instances of the RNA molecule in said sample, a quantitative measure of the relative or absolute number of intact instances of a selected segment of said RNA molecule, and the length of the selected segment.

The quantitative measure N of the relative or absolute number of instances of said RNA molecule in said sample may be given by:

$$N = N_i \cdot e^{+Lir}$$

Where $N_i$ is the number of instances of an intact segment of length L to the RNA molecule.

As detailed hereinbefore, in addition to the fact that the present inventors have developed a method of accurately quantitating the integrity of RNA, this determination in fact also enables one to use this result as a correction to adjust the results of a quantitative RNA analysis, of a gene of interest, to take into account the degree of RNA degradation present in the sample that was tested. This thereby enables one to obtain significantly more accurate results.

To this end, reference to an "RNA molecule of interest" should be understood as a reference to any RNA molecule that is transcribed from a DNA molecule or to any RNA molecule, such as RNA molecules which have an identity in their own right (i.e., not just as the template for a protein product) such as microRNA, tRNA, rRNA, siRNA, shRNA and the like. Accordingly, the RNA molecule of interest may or may not be one which is also translated to a protein product.

In one embodiment, the subject RNA is RNA transcribed from a gene of interest.

According to this embodiment, there is provided a method of quantifying the RNA transcribed from a gene of interest, said method comprising:

(i) assaying a sample containing instances of an RNA molecule transcribed from a reference gene, at least some of said instances being damaged, to determine quantitative measures of relative or absolute numbers of intact instances of each of a plurality of segments of said RNA molecule in said sample, said segments having respective different lengths;

(ii) based on a relationship between the determined quantitative measures and the respective different lengths of said segments, determining a quantitative measure of integrity of the instances of the RNA molecule in said sample; and (iii) quantifying the RNA transcribed from a gene of interest and correcting this result using the measure of integrity calculated in step (ii) and the length of a degradation-relevant segment of the RNA of interest.

In one embodiment, said RNA is mRNA.

Without limiting the present invention to any one theory or mode of action, reference to "quantifying", "quantification" or "quantitation" in accordance with the invention herein described is a reference to either absolute or relative quantification. Absolute quantification refers to the obtaining of an absolute number of RNA transcript copies, whereas relative quantification refers to quantification of the level of the RNA of interest in relation to the level of the RNA transcribed from a "standard gene" or an "RNA standard". These two terms are not necessarily antithetical.

Quantification of an RNA of interest generally involves two stages:

1. a measure is obtained of the absolute number of the RNA transcripts of interest in the sample;

1.1 if the measure is obtained by a direct method such as high-throughput RNA sequencing or digital PCR, which directly determine the number of the instances ($S_{test}$) of an intact segment of length L of the RNA transcript of interest, then the number of instances ($N_{test}$) of the RNA transcript of interest is given by:

$$N_{test} = S_{test} \cdot e^{+Lr}$$

where r is the measure of integrity of the RNA in the test sample;

1.2 if the measure is obtained indirectly, by using relative quantification involving an external RNA standard of known amount ($N_{stan}$) contained in a separate sample, then the number of instances ($N_{test}$) of the RNA transcript of interest is given by $$N_{test} = N_{stan} \cdot (S_{test}/S_{stan}) \cdot e^{(L_{test} \cdot r_{test} - L_{stan} \cdot r_{stan})}$$

where the subscripts "test" and "stan" refer to length (L) and measure of integrity (r) pertaining to the test and standard RNA, respectively. An example of the use of an external RNA standard, the mass of which is known, is quantification of BCR-ABL transcripts in chronic myeloid leukaemia. A measure is obtained of another gene such as BCR, both in the test sample and in an external standard sample. This enables determination of the absolute number of BCR transcripts in the test sample and thus a measure of the adequacy of the sample and the level of detection which is possible.

It should be appreciated by the person of skill in the art that where an external standard is to be used for the purpose of enabling quantification of the RNA expression levels of a gene of interest, it will be necessary for the RNA integrity of the external sample to be assessed, as well as the RNA integrity of the sample in which the transcription level of the gene of interest is to be analysed. In this way, both the quantification result of the standard and the gene of interest can be corrected to reflect the extent of RNA degradation of each individual sample. Occasionally, the external standard is added to the test sample and processed together with the RNA of interest, but its integrity must still be measured separately.

In practice, owing to the better stability of DNA, the "RNA" standard is most often substituted by a DNA standard which has the same sequence as a region of the RNA of interest, e.g., in the form of an insert in a plasmid. In theory, the integrity of the DNA should be assessed, but in practice the DNA is usually regarded as undamaged, i.e., the value of $r_{stan}$ is taken to be zero. If so:

$$N_{test} = N_{stan} \cdot (S_{test}/S_{stan}) \cdot e^{(L_{test} \cdot r_{test})}$$

1.3 if the measure is obtained indirectly, by not using an external standard and assuming that for all genes the measure ($S_{test}$) bears the same but unknown relationship to the number of instances of an intact segment of an RNA of interest, then the number of instances ($N_{test}$) of the RNA transcript of interest is given by:

$$N_{test} = k \cdot S_{test} \cdot e^{+Lr}$$

where k is a constant having a value which is unknown but is the same for all genes, and L is the length said segment. Although the value of N for any one gene is unknown, the ratio of the number of transcripts for any two genes (subscripts 1 and 2) is known since the constant k cancels out and $$N_1/N_2 = (S_1/S_2) \cdot e^{(L_1-L_2)r}$$

2. Performing relative quantification, whereby the measure of the absolute number of the RNA transcripts of interest in the sample previously obtained in 1.1, 1.2, or 1.3 above is expressed relative to a similarly obtained measure of the absolute number of the RNA transcripts of an internal standard RNA in the same sample. This procedure of relative quantification is sometimes referred to as normalisation. It is performed in an attempt to overcome the difficulty in relating the absolute number of instances of the RNA of interest in the sample to the absolute number of instances of the RNA of interest in the tissue of origin of the sample. This difficulty arises from variations in recovery of RNA, from the wide fluctuations in RNA levels which can occur in the tissue of origin in response to physiological or pathological changes, as the result of RNA degradation in vitro, or from absence of an actual value for an individual gene if quantification has been performed as in 1c above.

Relative quantification or normalisation is often expressed as the fold difference in expression of the RNA of interest relative to the internal standard. It will be appreciated by those skilled in the art that more than one gene of interest may be the subject of analysis in a given sample, such as where RNA expression profiles are being prepared, and each of these individual gene results can be assessed relative to the one standard result.

The method of this aspect of the present invention is likewise predicated on using the measure of integrity calculated in relation to the reference gene to correct the results obtained in respect of the gene of interest. Since the quantification of the RNA transcribed from the gene of interest is assessed relative to the transcription level of a standard gene, it would be appreciated that the correction is effectively applied to the results obtained for both the gene of interest and the standard gene. Generally, the standard gene and the reference gene used for determining RNA integrity will be two separate genes. However, it is conceivable that one might use the same RNA species for both the standard and the reference.

Since, in each case of sections 1.1, 1.2, and 1.3 above, the amount of the RNA molecule of interest in the sample is given by a relationship of the form $$N_{test} = \text{constant} \cdot S_{test} \cdot e^{+Lr}$$

the amount of the RNA molecule of interest in the sample relative to the amount of the internal standard RNA molecule in the sample is given by $$N_{test}/N_{stan} = (S_{test}/S_{stan}) \cdot e^{(L_{test}-L_{stan}) \cdot r}$$

where $N_{test}/N_{stan}$ is the ratio of the amount of the RNA molecule of interest (test molecule) to the amount of the standard RNA molecule, $S_{test}/S_{stan}$ is the ratio of the measured amounts of the respective test and standard segments in the sample, $L_{test}$ and $L_{stan}$ are the respective lengths of the test and standard degradation-relevant segments, and r is the mean number of lesions per nucleotide of the instances of the test and standard RNA molecules in the sample.

Reference to "correcting" is intended as a reference to the use of a measure of RNA integrity to convert a measure of the number of instances of an intact RNA molecule to an absolute or relative measurement of the total number of instances of said RNA molecule. It will be appreciated that an absolute or relative measurement of the total number of instances of said RNA molecule equals an absolute or relative measurement of the total number of instances of a segment of said RNA molecule.

To this end, reference to the RNA transcribed from a "standard gene" or an "RNA standard" is intended as a reference to the transcribed gene against which the RNA levels of interest are to be related and thereby quantified. It will be appreciated that in some circumstances of quantification an RNA standard may be substituted by a DNA standard having the same sequence as that portion of the RNA or cDNA of the gene of interest as is directly used for quantification. Without limiting the present invention to any one theory or mode of action, the genes suitable for use as the standard are preferably expressed at a high level. Even more preferably, the level of expression is not affected by the tissue of origin of the sample. However, as would be known by those of skill in the art, there are few genes which fulfil both these criteria. To this end, an alternative approach is to analyse a panel of standard genes. Generally, the standard gene and the reference gene will be two separate genes. However, it is conceivable that one might use the same RNA species for both the standard and the reference.

Reference to a "sample" should be understood as a reference to either a biological or a non-biological sample. Examples of non-biological samples include, for example, the nucleic acid products of synthetically produced nucleic acid populations. Reference to a "biological sample" should be understood as a reference to any sample of biological material derived from an animal, plant or microorganism (including cultures of microorganisms) such as, but not limited to, cellular material, blood, mucus, faeces, urine, tissue biopsy specimens, fluid which has been introduced into the body of an animal and subsequently removed (such as, for example, the saline solution extracted from the lung following lung lavage or the solution retrieved from an enema wash), plant material or plant propagation material such as seeds or flowers or a microorganism colony. The biological sample that is tested according to the method of the present invention may be tested directly or may require some form of treatment prior to testing. For example, a biopsy sample may require homogenisation prior to testing, or it may require sectioning for in situ testing. Further, to the extent that the biological sample is not in liquid form (if such form is required for testing), it may require the addition of a reagent, such as a buffer, to mobilise the sample.

To the extent that the target RNA is present in a sample, the sample may be directly tested, or else all or some of the nucleic acid material present in the sample may be isolated prior to testing. It is within the scope of the present invention for the target nucleic acid molecule to be pre-treated prior to testing, for example inactivation of live virus or being run on a gel. It should also be understood that the sample may be freshly harvested, or it may have been stored (for example by freezing) prior to testing, or otherwise treated prior to testing (such as by undergoing culturing).

The choice of what type of sample is most suitable for testing in accordance with the method disclosed herein will be dependent on the nature of the situation, such as the nature of the condition being monitored. For example, in one embodiment a neoplastic condition is the subject of analysis. If the neoplastic condition is a leukaemia, then a blood sample, lymph fluid sample or bone marrow aspirate would likely provide a suitable testing sample. Where the neoplastic condition is a lymphoma, then a lymph node biopsy or a blood or marrow sample would likely provide a suitable source of tissue for testing. Consideration would also be required as to whether one is monitoring the original source of the neoplastic cells, or whether the presence of metastases or other forms of spreading of the neoplasia from the point of origin is to be monitored. In this regard, it may be desirable to harvest and test a number of different samples from any one mammal. Choosing an appropriate sample for any given detection scenario would fall within the skills of the person of ordinary skill in the art.

The term "mammal", to the extent that it is used herein, includes humans, primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. kangaroos, deer, foxes). Preferably, the mammal is a human or a laboratory test animal. Even more preferably, the mammal is a human.

Figure 3:
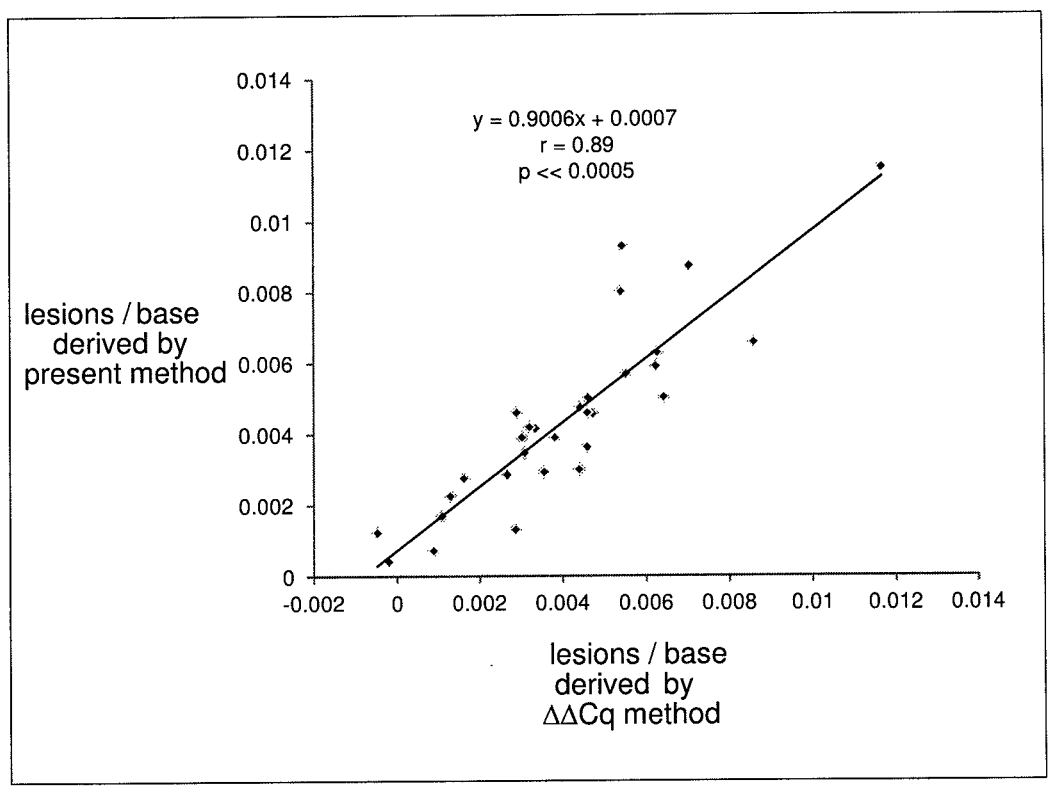
FIG. 3. Comparison between measuring RNA integrity by the present method, and by the $\Delta\Delta Cq$ method. The latter provides an independent benchmark against which the present method may be evaluated. The RNA in 30 samples was degraded by heat. The present method quantified degradation by studying the degraded sample only, whereas the $\Delta\Delta Cq$ method quantified degradation using the Cq difference between the degraded sample, and a control undegraded sample of the same RNA.
Figure 4:
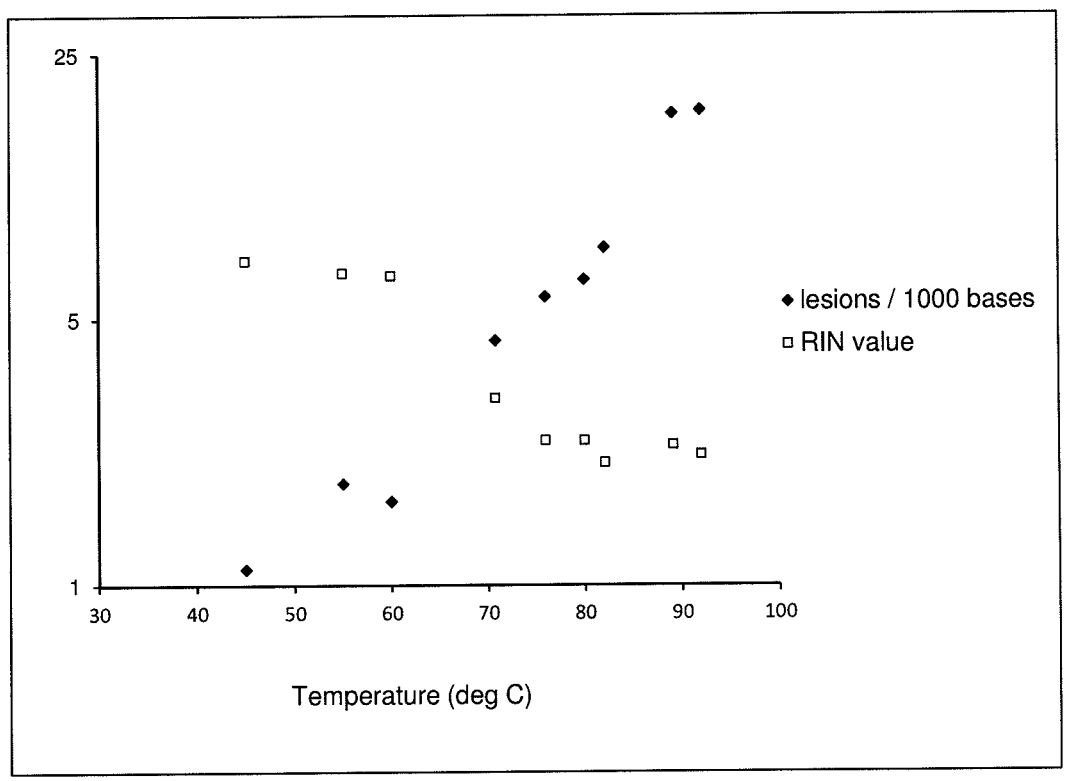
FIG. 4. Comparison between the present method for measuring lesions/base, and the standard RIN score, which is based on automated electrophoresis. Nine RNA samples were partially degraded by heating at various temperatures for 30 minutes, and then analysed. Shown are lesions/1000 bases and the RIN index, which ranges from 0 to 10. The number of lesions/base shows a progressive increase as the temperature of heating increases, whereas RIN shows a largely "all-or-nothing" step-like responses and is clearly not quantitative. RNA degraded to the extent that more than 5-6 lesions/1000 bases are present is concluded by RIN to be too degraded to analyse. However the present method is still able to quantify degradation and thus determine the level of an RNA of interest in samples judged too degraded by RIN.
Figure 5:
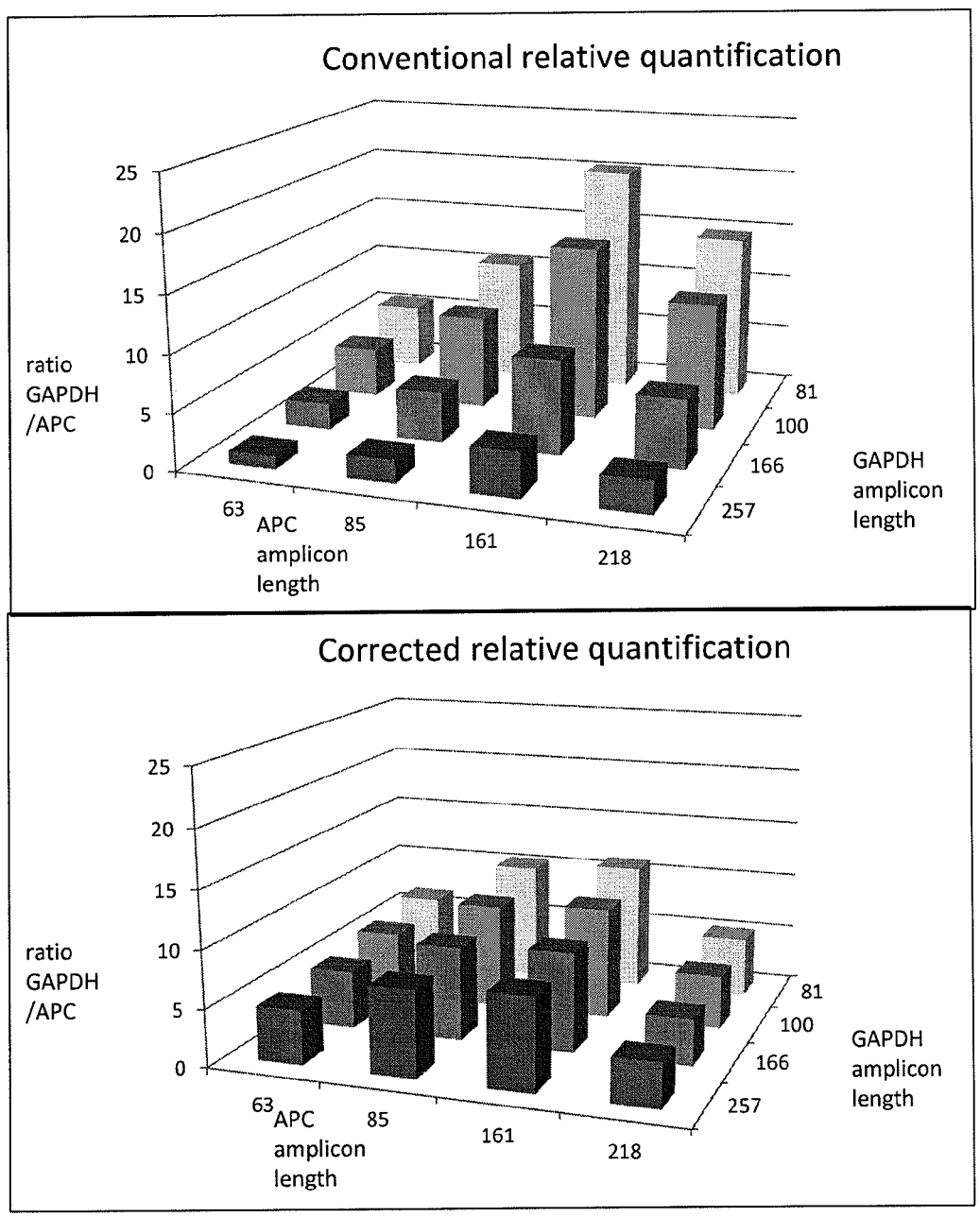
FIG. 5. Relative quantification of different lengths of GAPDH mRNA relative to different lengths of APC mRNA as the standard. Relative quantification was performed either by the conventional method or after quantifying degradation and then correcting the conventional ratio by using the equation on line 5 of page 35. The RNA was either control RNA or RNA degraded by heating at 91° C. for 30 minutes. The results obtained by conventional relative quantification are influenced by the length of the test amplicon, the length of the standard amplicon and the presence of degradation. These effects largely disappear after correction for degradation and length, any remaining variation being consistent with random experimental variation. For degraded RNA, in each experiment correcting the results of conventional relative quantification resulted in a highly significant (p<0.0005) decrease in their variance; for control RNA, correction produced a decrease in variance in each case, but the decreases were not significant.

The present invention has several advantages when compared to current methods. Unlike the latter, which are only qualitative, the method of the present invention is quantitative and thus enables the total number of RNA molecules of interest in a sample to be quantified, and over a wide range of degradation, as shown in FIG. 3. It is very sensitive, as only a very small amount of RNA is required. Data on sensitivity are shown in Example 1.

Another advantage of the present invention is that it provides a means to both determine a quantitative measure of RNA integrity of a sample and to thereafter accurately quantitate the RNA expression levels of a gene of interest, without the need to necessarily use an amplification protocol. Although many RNA analysis protocols are based on an application of PCR, RNA can in fact be quantified by a number of methods that do not involve nucleic acid amplification. The fact that the method of the present invention can be successfully adapted to any RNA analysis protocol, to enable the relative or absolute quantification of RNA to be corrected for degradation, is a significant step forward which has not previously been available. Without limiting the present invention in any way, variation in the 'degradation-relevant' or 'critical' length of an RNA segment (of value L), the degradation of which will influence the result, will occur in any method for which hybridisation occurs at one point along the RNA strand and quantification involves another point at a variable distance along the RNA strand, including, for example, the methods described below.

1. Micro-Arrays

DNA probes are spotted onto a solid surface and fluorescently-labelled RNA is contacted. Theoretically, degradation could be measured entirely by micro-array, by quantifying fluorescence at spots corresponding to two or more sequences along a reference gene, but this is very cumbersome and imprecise. Almost certainly, degradation would be quantified by an independent technique prior to the definitive micro-array study. The relative effect of degradation on quantification of the RNA of interest and the internal standard would then be determined both by the measure of degradation and the means by which the RNA has been isolated and hybridised. If the RNA has been isolated by polyT capture, then, for each of the two RNA species, the distance between the polyA sequence and the sequence to which the probe hybridises will affect quantification. If the RNA has been converted to cDNA by random priming, then the relative lengths of the two hybridising sequences will affect the result of quantification.

2. Nanostrings

Each species of RNA is captured by a gene-specific capture probe, hybridised to a fluorescently-labelled reporter probe, and electrophoresed. Theoretically, degradation could be quantified by this technique by using several reporter probes, each of which hybridised to a different sequence of a reference RNA. However, in practice, it would be much simpler to determine degradation by an independent method prior to the definitive nanostring study. The relative effect of degradation on quantification of the RNA of interest and the internal standard would then be determined both by the measure of degradation and, for each of the RNA of interest and the standard RNA, by the length of RNA between and containing the hybridisation sequence for the capture probe and the hybridisation sequence of the reporter probe.

3. SAGE

There are a number of variations of this technique. The RNA is captured by polyT and then digested by a restriction enzyme. A complicated sequence of manipulations then ensues, the final result being that the sequence next to the enzyme cutting site is identified by sequencing. Quantification is based on the number of times this sequence is manifest.

In practice, quantification of degradation by study of a reference gene is not practical by SAGE, and an independent technique is required. The relative effect of degradation on quantification of the RNA of interest and the internal standard would then be determined both by the measure of degradation and, for each of the RNA of interest and the standard RNA, by the length of RNA between and containing the polyA sequence and the restriction enzyme cutting sequence.

4. RNA Sequencing

High throughput RNA sequencing, in which an enormous number of reads can be obtained, is being increasingly used for RNA quantification. The final quantification recognises both intact and degraded RNA, and provides an absolute number without the necessity of an external standard. However, if the preparatory manipulation leading up to quantification by sequencing involves a length-dependent process, such as positive selection by polyT capture, which is affected by degradation, then degradation will need to be measured, either by quantifying the number of reads for a plurality of segments of a plurality of RNA molecules, or by using a separate method and involving a reference gene.

5. Nucleic Acid Amplification (e.g. qPCR)

The extent of degradation is simply and conveniently measured by qPCR of a reference gene, either by amplifying two or more amplicons of different length or, if the RNA has been captured by polyT, by amplifying two or more separate amplicons.

The relative effect of degradation on quantification of the RNA of interest and the internal standard would then be determined both by the measure of degradation and, for each of the RNA of interest and the standard RNA, by the lengths of the degradation-relevant segments, which depend on the method by which the cDNA has been produced.

Poisson Statistics

Damage to RNA may be quantified in terms of the mean number of lesions per base, with a lesion being defined as damage to an RNA molecule which prevents detection of that molecule by downstream quantification. The basic assumption is that lesions occur randomly and independently. This assumption seems undoubted when considering external physical or chemical agents, which damage RNA by hydrolytic, phosphorolytic or thermodynamic cleavage, or by the random production of adducts. However RNA can also be degraded by the action of a large number of ribonucleases, either endo-ribonucleases or exoribonucleases. Endoribonucleases may show some base or sequence specificity. But, in relation to the total RNA strand, bases and/or short sequences occur at random, so enzyme activity can also be regarded as random. The randomness or non-randomness of exoribonucleases is difficult to assess as there are many enzymes and a variety of mechanisms. However, for most exoribonucleases and for most RNA sequences, the RNA strand degraded by the enzyme is completely degraded, and we are not aware of any compelling evidence that this occurs in a non-random fashion. In view of the above considerations, we regard the great majority of RNA degradation as occurring randomly.

Since quantification only involves study of a segment of the RNA molecule, a damaging lesion will only affect quantification if it affects a base within this critical segment. The nature of this critical segment and the number of bases it comprises, the number being termed L, are determined by the technique used for RNA isolation and quantification. The probability that a given number of lesions will affect the critical segment is described by the binomial distribution. If the mean number of lesions/base in RNA is r, then the probability that there will be no lesions affecting an RNA segment of length L is $(1-r)^L$. When r is very small, the Poisson distribution provides a good approximation to the binomial distribution. The probability P(0) of no lesions in the segment is the zero term of a Poisson distribution whose expected value μ is the mean number of lesions in the strand. Thus:

$$P(0)=e^{-\mu}=e^{-Lr}$$

If N is the total number of mRNA molecules and $N_i$ is the number of intact and quantifiable molecules then $$N_i = N \cdot e^{-Lir}$$

and $$\ln(N_i) = \ln(N) - L_i \cdot r$$
$$= \text{constant} - L_i \cdot r$$

Thus, if a constant number of RNA molecules is assayed by performing two or more quantifications, each of which is based on a different and known value of L (but the same value of r), then the value of r can be determined, as it equals the slope of the regression line between $\ln(N_i)$ and L. Some methods, such as digital PCR and RNA sequencing, enable $N_i$ to be determined as an absolute number, but in most cases $N_i$ will not be determined as an absolute number, but rather will be measured in units, such as fluorescence for micro-array and nanostring, a number of sequences for SAGE, or Cq values for amplification methods. However, the relationship between the arbitrary unit and the number of molecules quantified still enables r to be determined. Thus, if the magnitude of fluorescence is proportional to the number of hybridising molecules, then:

$$\ln(\text{fluorescence})=\text{constant}-L\cdot r$$

and r equals the negative value of the slope of the regression line between fluorescence and L.

For cyclic amplification methods, $$N_t=N_i \cdot a^{Cq}$$

where $N_t$ is the number of molecules at threshold, a is the amplification efficiency in terms of the amplification factor of each amplification cycle, and Cq is the number of cycles to threshold. Since $N_t$ is a constant number:

$$\ln(N_i)=\ln(N_t/a^{Cq})=\text{constant}-L\cdot r$$

and rearranging: $\ln(N_t)-\ln(a)\cdot Cq=\text{constant}-Lr$ hence: $Cq=\text{constant}'+L\cdot r/\ln(a)$ For different values of L, a can be regarded as constant, provided that the chosen amplification system is efficient. Determination of the slope of the regression line between Cq and L then enables r to be calculated as $$r=\text{slope}\cdot\ln(a)$$

The value of L depends upon the technique used for RNA isolation and quantification, as illustrated in FIG. 1. For quantification by nanostring technology, L is the number of bases between the outermost base of the sequence hybridising to the capture probe and the outermost base of the sequence hybridising to the reporter probe. For quantification by serial analysis of gene expression (SAGE), L is the number of bases between the outermost base of the sequence hybridising to the polydT capture probe and the base immediately adjacent to the restriction enzyme cutting site. For quantification by micro-array technology, if the cDNA is labelled using polydT as a primer, then the value of L is the number of bases between the outermost base of the sequence hybridising to the polydT primer and the outermost base of the sequence hybridising to the DNA probe on the micro-array, whereas if the cDNA is labelled using random priming, then the value of L is the number of bases between the outermost base of the sequence defined by the mean point at which the random primers hybridise and the outermost base of the sequence hybridising to the DNA probe on the micro-array. For quantification by RNA sequencing and cDNA synthesis by polydT priming, the value of L is the number of bases between the most 5' T base and the most 3' base on the same strand of the read. For quantification by nucleic acid amplification technology, if the cDNA is produced using polydT or a gene-specific primer, then the value of L is the number of bases between the outermost base of the sequence hybridising to the polydT primer or the gene-specific primer and the outermost base of the sequence hybridising to the upstream DNA primer, whereas if the cDNA is labelled using random priming, then the value of L is the number of bases between the outermost base of the sequence defined by the mean point at which the random primers hybridise and the outermost base of the sequence hybridising to the upstream DNA amplification primer.

Figure 2:
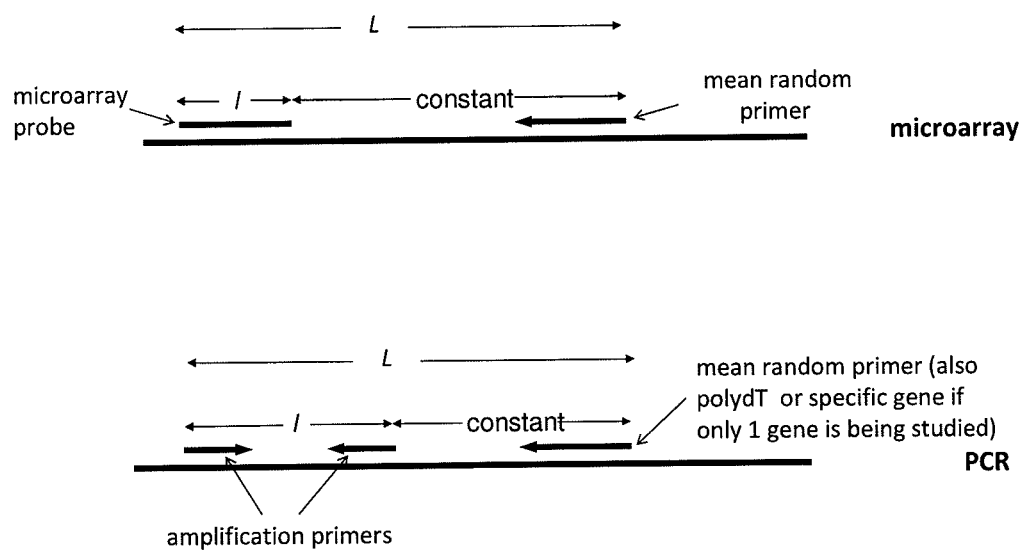
FIG. 2. Relationship between L and l. When the critical region of length L has a constant region and a variable region of length l, the value of l may be used as a surrogate for L. This applies for some situations of quantification by microarray or PCR.

In some situations, the value of L may consist of a constant component and a random component. The value of L is known when RNA is isolated by probe capture, or when cDNA is produced by polydT or gene-specific priming, but it is not known when cDNA is produced by random priming. However, with random priming, the length L can be regarded as being made up of two components: a constant component which represents the mean length of cDNA stretching from a random primer to the point of measurement, and a variable component (of length l) which represents the sequence utilised for measurement, as shown in FIG. 2. When cDNA is produced by random priming for micro-array hybridisation, the variable component is the length of sequence which hybridises to the DNA probe; when cDNA is produced by variable priming for quantification by PCR or other forms of nucleic acid amplification, the random component is the length of the amplicon. For polydT or gene-specific priming, although the value of L is known, in some cases it may be convenient to similarly regard L as having a constant and a variable component. The constant component of the cDNA stretches from the most 5' T base to the base adjoining the most proximal sequence which is the target for amplification; the distal sequence for each segment is the variable component. Again:

$$L = l + \text{constant}$$

and l can be substituted for L in the relevant equation (s), the only change being a change in the value of the constant, and $$Cq = \text{constant} + l \cdot r / \ln(a)$$

and r can still be calculated from the slope of the regression line between Cq and l, as $$r = \text{slope} \cdot \ln(a)$$

Once the value of r is known, results of RNA quantification can be corrected for degradation.

In view of the above, the variable sequence of length l should be understood as a derivative of the degradation-relevant sequence of length L, and it should be understood that this derivative can substitute for the degradation-relevant sequence and that its length l can substitute for L in the relevant formulae related to integrity.

In the great majority of cases, an RNA species of interest is quantified relative to an internal standard RNA. If $N_{test}$ is the total number of molecules of the test RNA, $N_{stan}$ is the total number of molecules of the standard RNA, test is the result of the quantification of the test RNA expressed as a number which is proportional to the number of molecules quantified, and standard is the result of quantification of the standard RNA, also expressed as a number which has the same proportionality to the number of molecules quantified, then:

$$\text{test/standard} = N_{test} \cdot e^{-L_{test} \cdot r} / N_{stan} \cdot e^{-L_{stan} \cdot r}$$

and hence $$N_{test}/N_{stan} = (\text{test/standard}) \cdot e^{(L_{test} - L_{stan}) \cdot r}$$

Or, in situations where l is applicable, $$N_{test}/N_{stan} = (\text{test/standard}) \cdot e^{(l_{test} - l_{stan}) \cdot r}$$

A number of RNA species are sometimes used to provide the result for the standard. In this situation, the mean length of L or l should be used.

In a small minority of cases, an RNA of interest is quantified relative to an external standard of the same RNA. In this case, the values of L and the values of r may differ. Thus:

$$N_{test}/N_{stan} = (\text{test/standard}) \cdot e^{(L_{test} \cdot r_{test} - L_{stan} \cdot r_{stan})}$$

If the values of L are the same:

$$N_{test}/N_{stan} = (\text{test/standard}) \cdot e^{(r_{test} - r_{stan})L}$$

The method of the present invention has application in a wide variety of clinical and research scenarios. For example, obtaining an RNA expression profile (i.e., quantifying the expression of hundreds or thousands of genes) is much more commonly performed than quantifying the expression of a single gene. From the research point of view, it can provide information on intracellular regulatory networks, on identification of genes which are important in intracellular processes, and on the effects of external agents on the cell. The information so obtained may identify targets which might be susceptible to therapeutic intervention or may elucidate the mode of action of therapeutic drugs. From the diagnostic point of view, RNA expression profiling can identify new subgroups of leukaemia or other forms of cancer, and has been the only method for determining the tissue of origin of some instances of cancer, thus enabling appropriate tissue-specific treatment to be applied.

With regard to quantifying a single gene, chronic myeloid leukaemia is an example where a specific RNA provides a tumour-specific marker, and, in this disease, quantification of BCR-ABL is used to guide and adjust treatment and to determine prognosis.

The methods described above can, in general, be performed manually or by automated or semi-automated systems. For example, robotic RNA expression profiling systems can be configured to perform the methods described above in order to perform RNA expression profiling, where the results of profiling are automatically corrected for degradation as described above. Alternatively, the correction(s) can be performed as a separate step to correct RNA expression profiling data that has been acquired at an earlier time. In such cases, the uncorrected RNA expression profiling data may be stored locally, on the same or on a different computer system, or may be retrieved from a remotely located system via a communications network, which may be the Internet, for example.

The correction of RNA expression profiling data (either separately, or essentially simultaneously with the acquisition of RNA expression profiling data) is particularly useful when performed automatically or in a 'batch' mode on large data sets, such as when profiling a plurality of transcripts from a plurality of genes, for example.

Figure 6:
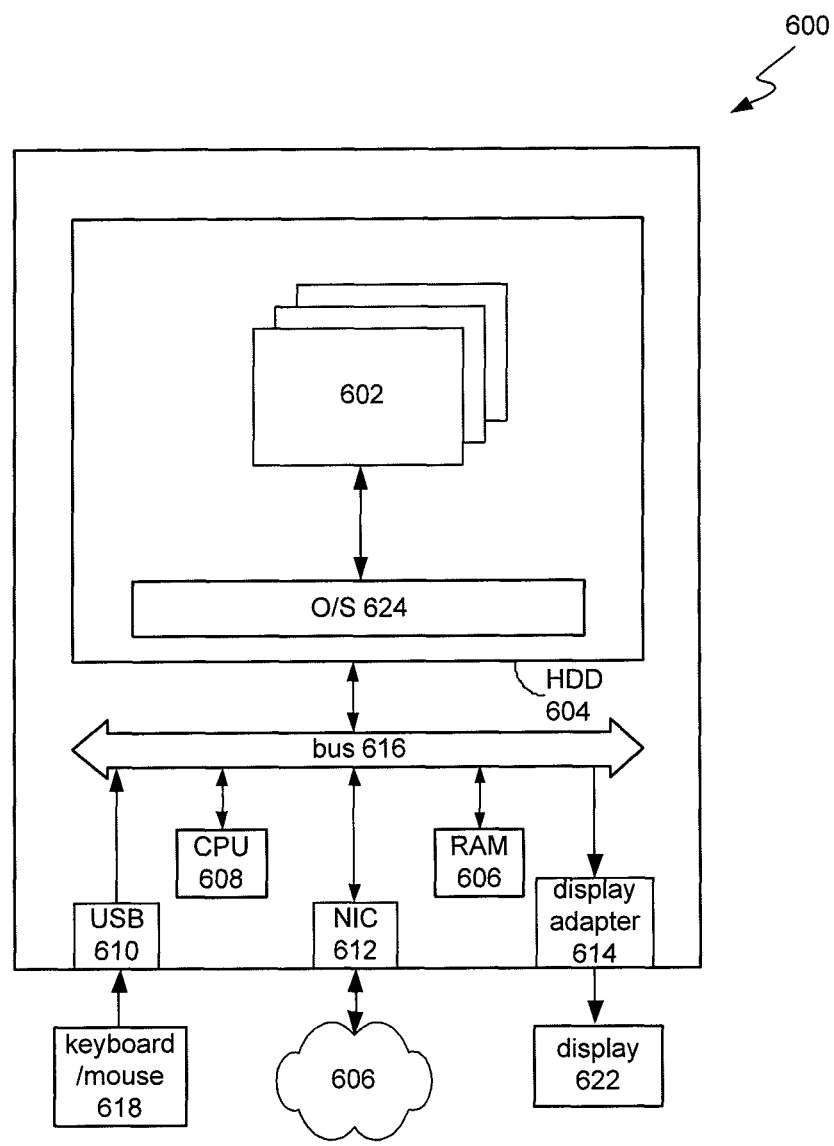
FIG. 6. Schematic block diagram of a data processing system for use in RNA expression profiling based on quantitative integrity measures as described herein.

In general, the methods described herein may therefore be embodied in a data processing system which may or may not include robotic components for automatically performing assays according to inputs provided by a user of the system. By way of example, in one embodiment, the data processing system is a standard computer system such as a 32-bit or 64-bit Intel Architecture computer system 600, as shown in FIG. 6, and the methods executed by the system 600 are implemented in the form of programming instructions of one or more software modules or components 602 stored on non-volatile (e.g., solid-state or hard disk) storage 604 associated with the system 600, as shown in FIG. 6. However, it will be apparent to those skilled in the art that the methods could alternatively be implemented, either in part or in their entirety, in the form of one or more dedicated hardware components, such as application-specific integrated circuits (ASICs), and/or in the form of configuration data for configurable hardware components such as field programmable gate arrays (FPGAs), for example.

The system 600 shown in FIG. 6 includes standard computer components, including random access memory (RAM) 606, at least one processor 608, and external interfaces 610, 612, 614, all interconnected by a bus 616. The external interfaces include universal serial bus (USB) interfaces 610, at least one of which is connected to a keyboard 318 and pointing device such as a mouse, a network interface connector (NIC) 612 which connects the system 300 to a communications network 620 such as the Internet, via which RNA expression profile data can be accessed by the system 600. The system 300 also includes a display adapter 314, which is connected to a display device such as an LCD panel display 322, and a number of standard software modules 626 to 630, including an operating system 624 such as Linux or Microsoft Windows.

Thus in some embodiments, the components 602 are configured to:

(i) retrieve or otherwise access stored RNA expression profiling data representing standard quantification of at least one RNA molecule;

(ii) retrieve or otherwise access stored RNA integrity data representing a quantitative measure of integrity of the instances of each said RNA molecule;

(iii) retrieve or otherwise access stored length data representing one or more lengths of corresponding degradation-relevant segments (or derivatives thereof) of the RNA molecule; and (iv) process the RNA expression profiling data, the RNA integrity data and the length data to generate corrected RNA expression profiling data representing corrected values of said quantification of said at least one RNA molecule.

The RNA expression profiling data or the RNA integrity data (or both) may be generated by the system 600 itself, or may be received from another system. As described above, the degradation-relevant segment of an RNA molecule (and hence its length) is determined by the expression profiling method used to generate the RNA expression profiling data, and therefore the latter will usually be stored in association with the length data, although this need not necessarily be the case.

In some embodiments, the components 602 are configured to cause the system 600 to:

(i) assay a sample containing instances of an RNA molecule transcribed from a reference gene, at least some of said instances being damaged, to determine quantitative measures of the relative or absolute numbers of intact instances of each of a plurality of segments of said RNA molecule in said sample, said segments having respective different lengths, to generate assay data representing said quantitative measures and said lengths; and (ii) processing said assay data to generate integrity data representing a quantitative measure of integrity of the instances of said RNA molecule in said sample, based on a relationship between the determined quantitative measures and the respective different lengths of said segments.

In some embodiments, the components 602 are further configured to cause the system 600 to:

(iii) quantify the RNA of interest and correct this result using the measure of integrity calculated in step (ii) and the length of a corresponding degradation-relevant segment of the RNA of interest.

The present invention is further described by reference to the following non-limiting example.

Example

TABLE 1

Investigation into the least amount of mRNA which is required for quantification of degradation. In practice, the amount of mRNA available for study is often limited and/or the mRNA may be more or less degraded. Both of these factors interact and may affect the ability to quantify mRNA. In this series of experiments, the mRNA was control mRNA or mRNA degraded by heating. Integrity was measured using the GAPDH gene. The control estimate for integrity was obtained from analysis of the greatest mass of RNA analysed, and the estimate at the limit was obtained from analysis of the least mass of RNA that provided a reliable regression line between Cq and amplicon length. The conventional RIN method for assessing degradation only classifies an RNA sample as being suitable or unsuitable for analysis, requires at least 50 pg of RNA, and concludes that RNA quantified with the present method as having more than 5-6 lesions/1000 bases is too degraded to analyse. The present method overcame the deficiencies of RIN. Overall, gene-specific priming appeared superior to random priming, although it was slightly less sensitive when the RNA was only slightly degraded.

| degradation | | minimal pg | lesions/1000 bases | |
|---|---|---|---|---|
| °C. for 30 min. | priming | RNA providing quantification | best estimate | estimate at limit |
| Control | random | <16 | 1.1 | −0.2 |
| control | random | 1 | 1.4 | 1.4 |
| 85 | random | 16 | 3.9 | 2.3 |
| 88 | random | 63 | 7.5 | 7.8 |
| 91 | random | 126 | 9.7 | 27.9 |
| 91 | Gene-specific | 10 | 9.7 | 9.0 |
| 91 | Gene-specific | 10 | 9.4 | 4.3 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method of determining a quantitative ratio-scale measure of integrity of RNA in a single sample containing instances of an RNA molecule, at least some of said instances being damaged, said method comprising:

(i) assaying quantitative measures of relative or absolute numbers of intact instances of each of a plurality of degradation-relevant segments of said RNA molecule in said single sample, and determining respective different lengths of said segments; and (ii) applying a statistical relationship between the integrity of the instances of said RNA molecule, the determined quantitative measures and the respective different lengths of said segments to obtain the quantitative ratio-scale measure of integrity of the instances of said RNA molecule in said single sample.

2. The method of claim 1, further comprising:

(iii) quantifying an RNA of interest and applying the measure of integrity calculated in step (ii) and the length of a corresponding degradation-relevant segment, or derivative thereof, to obtain a corrected quantification of the RNA of interest.

3. The method of claim 1, further comprising:

(iii) quantifying an RNA of interest transcribed from a standard gene and applying the measure of integrity determined in step (ii) and the length of a corresponding degradation-relevant segment, or derivative thereof, to obtain a corrected quantification of the RNA of interest.

4. The method of claim 1, further comprising determining quantitative measures of relative or absolute numbers of total instances of a plurality of segments of said RNA molecule in said single sample which is to be quantified relative to a standard RNA molecule wherein a ratio of a total number $N_{test}$ of said RNA molecule in said single sample to a total number $N_{stan}$ of the standard RNA molecule is given by:

$$N_{test}/N_{stan}=(S_{test}/S_{stan}) \cdot e^{(L_{test} \cdot r_{test} - L_{stan} \cdot r_{stan})}$$

where $S_{test}$ and $S_{stan}$ are the respective quantitative measures of the relative or absolute numbers of intact segments of said RNA molecule in said single sample and the standard RNA molecule, $L_{test}$ and $L_{stan}$ are respective lengths of degradation-relevant segments, or derivatives thereof, of said RNA molecule in said single sample and the standard RNA molecule, and $r_{test}$ and $r_{stan}$ are respective ratio-scale measures of integrity of said RNA molecule in said single sample and the standard RNA molecule comprising mean numbers of lesions per nucleotide.

5. The method of claim 1, wherein the statistical relationship comprises a relationship between a number (N) of the instances of said RNA molecule in said single sample, the quantitative measures of the relative or absolute numbers ($N_i$) of intact instances of each of a plurality of segments i of said RNA molecule in said single sample, corresponding lengths ($L_i$) of said segments, and a mean number (r) of lesions per nucleotide of the instances of said RNA molecule in said single sample, given by:

$$N_i = N \cdot e^{-L_i r}.$$

6. The method of claim 1, wherein the statistical relationship comprises a relationship between a number (N) of the instances of said RNA molecule in said single sample, the quantitative measures of the relative or absolute numbers ($N_i$) of intact instances of each of a plurality of segments i of said RNA molecule in said single sample, corresponding lengths ($L_i$) of said segments, and a mean number (r) of lesions per nucleotide of the instances of said RNA molecule in said single sample, given by:

$$\ln(N_i) = \ln(N) - L_i \cdot r$$

and wherein the method further comprises determining a gradient of a linear relationship between $\ln(N_i)$ and $L_i$ for said plurality of segments i in order to determine r as the quantitative ratio-scale measure of integrity of the instances of said RNA molecule in said single sample.

7. A method for determining a quantitative measure of relative or absolute numbers of total instances of a plurality of segments of at least one RNA molecule of interest in a single sample containing instances of one or more RNA molecules, at least some of said instances being damaged, said method comprising:
  (a) accessing RNA expression profiling data representing a conventional quantification of each said RNA molecule in said single sample;
  (b) obtaining RNA integrity data representing a quantitative ratio-scale measure of integrity of the instances of the at least one said RNA molecule of interest in said single sample, by a method comprising:
    (i) assaying quantitative measures of relative or absolute numbers of intact instances of each of a plurality of degradation-relevant segments of said at least one RNA molecule of interest in said single sample, and determining respective different lengths of said segments; and
    (ii) applying a statistical relationship between the integrity of the instances of said at least one RNA molecule of interest, the determined quantitative measures and the respective different lengths of said segments to obtain the quantitative ratio-scale measure of integrity of the instances of said at least one RNA molecule of interest in said single sample,
  (c) accessing length data representing one or more lengths of respective degradation-relevant segments, or derivatives thereof, of said at least one RNA molecule of interest in said single sample; and
  (d) processing the RNA expression profiling data, the RNA integrity data and the length data to generate corrected RNA expression profiling data representing corrected values of said quantification of said at least one RNA molecule of interest in said single sample.

8. A method for use in determining a quantitative ratio-scale measure of integrity of RNA in a single sample containing instances of an RNA molecule, at least some of said instances being damaged, said method comprising:
  (i) assaying quantitative measures of relative or absolute numbers of intact instances of each of a plurality of degradation-relevant segments of said RNA molecule in said single sample, and determining respective different lengths of said segments, to generate assay data representing said quantitative measures and said lengths; and
  (ii) processing said assay data to generate integrity data representing a quantitative ratio-scale measure of integrity of the instances of said RNA molecule in said single sample, by applying a statistical relationship between the integrity of the instances of said RNA molecule, the determined quantitative measures and the respective different lengths of said segments.

9. The method of claim 8, further comprising:
  (iii) quantifying an RNA of interest; and
  (iv) applying the measure of integrity determined in step (ii) and the length of a corresponding degradation-relevant segment, or derivative thereof, to obtain a corrected quantification of the RNA of interest.

10. The method of claim 1, wherein said RNA is mRNA.

11. The method of claim 1, wherein each determined respective length has a constant component and a variable component.

12. The method of claim 1, wherein each determined respective length is a statistical average of a plurality of different lengths.

13. A non-transitory computer-readable storage medium having stored thereon executable instructions that, when executed by at least one processor of a data processing system, cause the at least one processor to execute a method for use in determining a quantitative ratio-scale measure of integrity of RNA in a single sample containing instances of an RNA molecule, at least some of said instances being damaged, said method comprising:
  (i) accessing assay data representing quantitative measures of relative or absolute numbers of intact instances of each of a plurality of degradation-relevant segments of said RNA molecule in said single sample, said segments having determined respective different lengths, said assay data comprising said quantitative measures and said lengths; and
  (ii) processing said assay data to generate integrity data representing a quantitative ratio-scale measure of integrity of the instances of said RNA molecule in said sample, by applying a statistical relationship between the integrity of the instances of said RNA molecule, the determined quantitative measures and the respective different lengths of said segments.

* * * * *